(12) United States Patent
Flohr et al.

(10) Patent No.: US 8,258,211 B2
(45) Date of Patent: Sep. 4, 2012

(54) PROCESS FOR MAKING MATERIAL FOR ACQUISITION OF LIQUIDS AND DISPOSABLE ABSORBENT ARTICLE COMPRISING THE MATERIAL

(75) Inventors: Andreas Flohr, Kronberg (DE); Marion Lutsche, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/177,665

(22) Filed: Jul. 7, 2011

(65) Prior Publication Data

US 2011/0259536 A1  Oct. 27, 2011

Related U.S. Application Data

(62) Division of application No. 12/061,164, filed on Apr. 2, 2008, now Pat. No. 7,994,242.

(30) Foreign Application Priority Data

Apr. 4, 2007 (EP) .................................... 07105640

(51) Int. Cl.
*C08L 1/02* (2006.01)
*D21H 11/20* (2006.01)
(52) U.S. Cl. ..... 524/35; 527/311; 162/164.1; 162/164.6
(58) Field of Classification Search .................. 527/311; 162/164.1, 164.6; 524/35
See application file for complete search history.

(56) References Cited

U.S. PATENT DOCUMENTS

| 3,860,003 A | 1/1975 | Buell et al. |
| 3,914,409 A | 10/1975 | McGahren et al. |
| 4,076,663 A | 2/1978 | Masuda et al. |
| 4,536,595 A | 8/1985 | Gardano et al. |
| 4,657,537 A | 4/1987 | Zimmerer |
| 4,834,735 A | 5/1989 | Alemany et al. |
| 5,037,416 A | 8/1991 | Allen et al. |
| 5,151,092 A | 9/1992 | Buell et al. |
| 5,256,746 A | 10/1993 | Blankenship et al. |
| 5,269,775 A | 12/1993 | Freeland et al. |
| 5,549,791 A * | 8/1996 | Herron et al. ............... 162/157.6 |
| 5,569,234 A | 10/1996 | Buell et al. |
| 5,650,222 A | 7/1997 | DesMarais et al. |
| 6,004,306 A | 12/1999 | Robles et al. |
| 2003/0144379 A1 | 7/2003 | Mitchell et al. |
| 2005/0004415 A1 | 1/2005 | Bull et al. |
| 2005/0065487 A1 * | 3/2005 | Graef et al. ................... 604/358 |

FOREIGN PATENT DOCUMENTS

| EP | 0 210 756 A1 | 6/1986 |
| EP | 1 291 460 A1 | 3/2003 |
| JP | 57-35938 A2 | 2/1982 |
| JP | 01-164436 A2 | 6/1989 |
| JP | 11-89878 A2 | 7/1989 |
| WO | WO 92/20735 | 11/1992 |
| WO | WO 95/34710 | 12/1995 |
| WO | WO 98/37149 | 8/1998 |
| WO | WO 99/33843 | 7/1999 |

OTHER PUBLICATIONS

EPO Search Report and Opinion, EP 07 10 5640, 2007.
International Search Report, PCT/IB2008/051240, mailed Jul. 31, 2008.

* cited by examiner

*Primary Examiner* — Tae H Yoon
(74) *Attorney, Agent, or Firm* — Abbey A. Lopez; Amy M. Foust

(57) ABSTRACT

A process for making a material for acquisition of liquids comprising individualized, crosslinked cellulosic fibers having an effective amount of a polymeric acid crosslinking agent reacted with the fibers in intra-fiber crosslink ester bond form. A process for making disposable absorbent articles, such as diapers, containing this material.

19 Claims, 2 Drawing Sheets

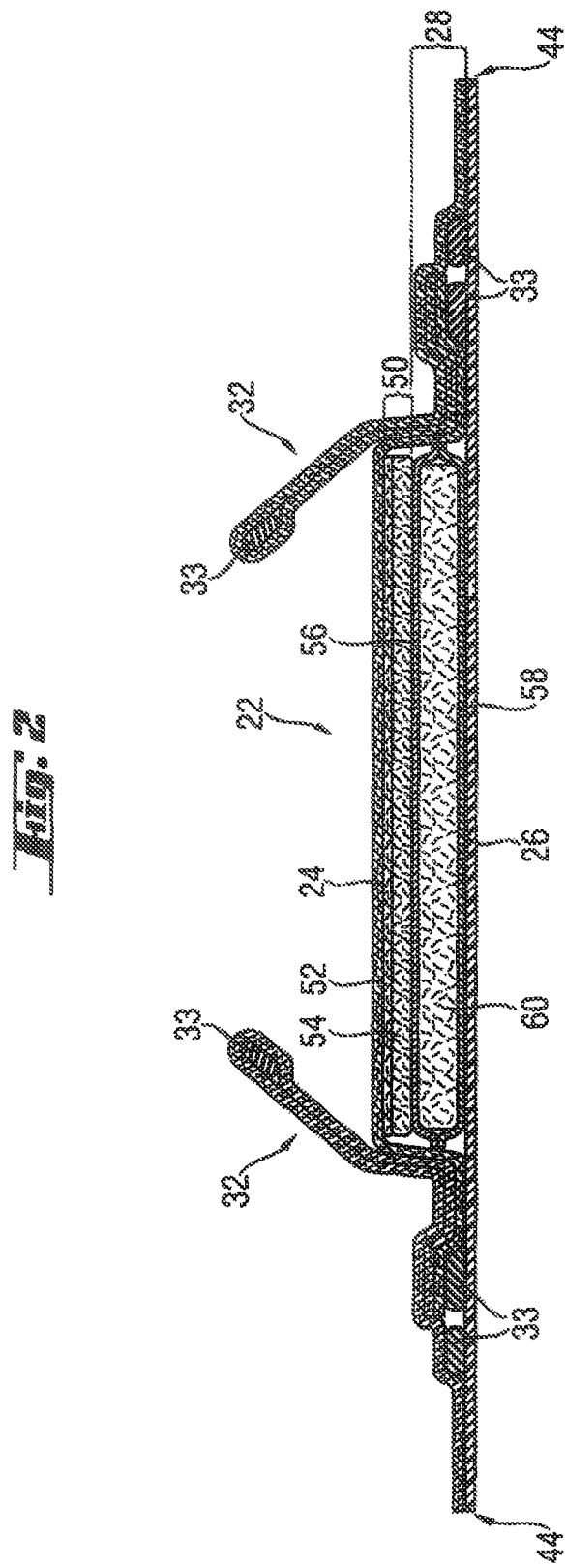

ately bonded carboxyl groups. One desirable
PROCESS FOR MAKING MATERIAL FOR ACQUISITION OF LIQUIDS AND DISPOSABLE ABSORBENT ARTICLE COMPRISING THE MATERIAL

CROSS REFERENCE TO RELATED APPLICATIONS

This application is a divisional of U.S. patent application Ser. No. 12/061,164, filed Apr. 2, 2008 now U.S. Pat. No. 7,994,242, which claims priority to EP 07105640.2, filed Apr. 4, 2007, each of which is hereby incorporated by reference in its entirety.

FIELD OF THE INVENTION

The present invention relates to a process for making material for acquisition of liquids, absorbent articles containing this material and methods for reducing the electrolyte concentration of aqueous mediums. The material comprises individualized, cellulosic fibers crosslinked with a polymeric acid and the material comprises at least one basic polymer.

BACKGROUND OF THE INVENTION

Disposable absorbent articles are broadly available and consumers are used to a high performance for the collection and retention of menses (in the case of sanitary napkins or panty liners) or for the collection and retention of urine and fecal material (in the case of e.g. disposable diapers). However, consumers do not only expect a superior absorbency behaviour, but place more and more emphasis on the wearing comfort of such articles, and namely on the dryness of those articles. Typically, such articles comprise multiple absorbent layers, at least one layer being primarily designed to store liquid (storage layer), and at least one other layer primarily designed to acquire and/or distribute liquid (acquisition layer). The storage layer may include super-absorbent material that is admixed with the traditionally used pulp fiber material. Such super-absorbent materials may be adapted to absorb many times (e.g. 10, 20, or 30 times) their own weight, and therefore be desirable when designing an article of improved fluid handling properties. Recent absorbent articles may employ higher concentrations of super-absorbent material than absorbent articles of the past, for example concentrations of superabsorbent material in excess of 50% of the total weight of the storage member. These products may achieve a relatively high absorbing capacity with a relatively thin storage member, thereby potentially reducing the overall thickness of the absorbent article product. While super-absorbent materials may be capable of storing substantial amounts of liquid, they may not able to distribute the liquid from the point of impact to more remote liquid storage areas of the absorbent article as fast as the liquid is discharged to the article. For this reason acquisition layers may sometimes be included in an absorbent article. Acquisition layers are typically configured to provide for the interim acquisition of liquid and for the distribution of liquid to various regions of the storage layer. After the initial acquisition of liquid by the acquisition layer, the liquid may subsequently be absorbed by and finally stored in the storage layer. Thus, the acquisition layer may provide a desirable way to maximize the absorbent capacity of the storage layer. An example of an acquisition layer is disclosed in PCT Publication No. WO 95/34710.

Besides initial acquisiton and distribution of liquids, another factor that may be considered when evaluating the performance of disposable absorbent articles is the absorbent capacity of the super-absorbent material in the storage layer. Super-absorbent materials may be provided in the form of super-absorbent polymers (SAPs), which are lightly crosslinked hydrophilic polymers that can absorb up to about one hundred times their own weight, or more, of distilled water. One commonly used SAP for absorbing electrolyte-containing liquids such as urine, is partially crosslinked, neutralized polyacrylic acid including for example 50% to 75% or 70% to 100% neutralized carboxyl groups. One desirable quality of an SAP in a hygienic article, such as a diaper, may include the ability to retain the absorbed fluid under a confining pressure. In at least some instances, the swelling and absorbent properties of SAPs may be attributed to (a) electrostatic repulsion between the charges along the polymer chains, and (b) osmotic pressure of the counter ions. However, it is commonly known in the art that these absorption properties are reduced in solutions containing electrolytes, such as saline, urine or blood. Thus, SAPs may function less effectively in the presence of such physiologic fluids. This decrease in absorption capacity is often referred to as "salt poisoning".

There have been attempts to couteract the salt poisoning effect by removing salts. For example, see US 2003/0144379 to Mitchell, et al.; PCT Publication No. WO 99/33843 to Garoff, et al.; PCT Publication No. WO98/37149 to Goldman; WO 92/20735 to Tanaka, et al.; EP 0 210 756 A1 to Wong; JP 57-35938 A2; JP 11-89878 A2; and JP 01-164436 A2.

Besides salt poisoning, the absorption capacity of SAPs may also be reduced by reducing the degree of neutralization, e.g. by acidifying liquids. U.S. Pat. No. 4,657,537 describes a disposable absorbent articles having an ion-exchanging topsheet. This topsheet exchanges only cations against protons. It does not remove anions and it acidifies the liquid by lowering the pH.

It may be desirable to provide material for the acquisition of electrolyte containing liquids with good acquisition, distribution and/or absorption properties. It may also be desirable to provide an improved acquisition material based on acid crosslinked cellulosic fibers which reduce the electrolyte concentration of a liquid without acidifying the liquid.

SUMMARY OF THE INVENTION

In some aspects, the present disclosure relates to a process for making a material for acquisition of liquids, said material comprising individualized, crosslinked cellulosic fibers including an effective amount of at least one acidic crosslinking agent reacted with said fibers in intra-fiber crosslink ester bond form, said acidic crosslinking agent being a polymer comprising a plurality of acidic functional groups; and at least one basic polymer or at least one conductivity reducing substance. The method may comprise providing a cellulosic based fiber. The method may comprise impregnating the fiber with the at least one acidic crosslinking agent and with the at least one basic polymer or at least one conductivity reducing substance. The method may comprise heating the resulting mixture to temperatures of at least the boiling point of water. The method may comprise baling the crosslinked fiber mixture. The cellulosic based fiber may be provided in slurry or unsheeted form. The cellulosic fiber may be provided in wet lap, dry lap, or other sheeted form. The method may comprise mechanically disintegrating a sheet.

The cellulosic based fiber may be selected from the group consisting of digested fibers from softwood, hardwood or cotton linters; fibers from Esparto grass; fibers from bagasse; fibers from kemp; and fibers from flax. The method may comprise moistening the cellulosic based fibers. The acidic functional groups may be selected from the group consisting of carboxylic acid, sulfonic acid, phosphoric acid, carboxylic acid, and combinations thereof. The acidic crosslinking agent may be polyacrylic acid, polyacrylic acid copolymers, or a combination thereof. The acidic crosslinking agent may be a copolymer of polyacrylic acid and maleic acid. The acidic crosslinking agent is a copolymer of low molecular weight monoalkyl substituted phosphinate and phosphonate. The acidic crosslinking agent may be used in combination with one or more other polycarboxylic acids. The at least one acidic crosslinking agent may be contacted with the cellulosic based fibers in a liquid medium. The at least one acidic crosslinking agent may be contacted with the cellulosic based fibers by spraying, spray and press, or dip and press processes.

The method may comprise mechanically difibrating the cellulosic based fiber into fluff. The method may comprise neutralizing non-reacted, free acid groups in the crosslinked fiber mixture. The non-reacted, free acid groups may be neutralized when the fibers are wetted. The non-reacted, free acid groups may be neutralized by a basic polymer, alone or in combination with other water soluble, non-polymeric bases.

The method may comprise incorporating the crosslinked fiber mixture into an absorbent article. The crosslinking fiber mixture may form at least a part of a liquid acquisition material.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

FIG. 2 is a cross-sectional view of the disposable diaper shown in FIG. 1

DETAILED DESCRIPTION OF THE INVENTION

Figure 1:
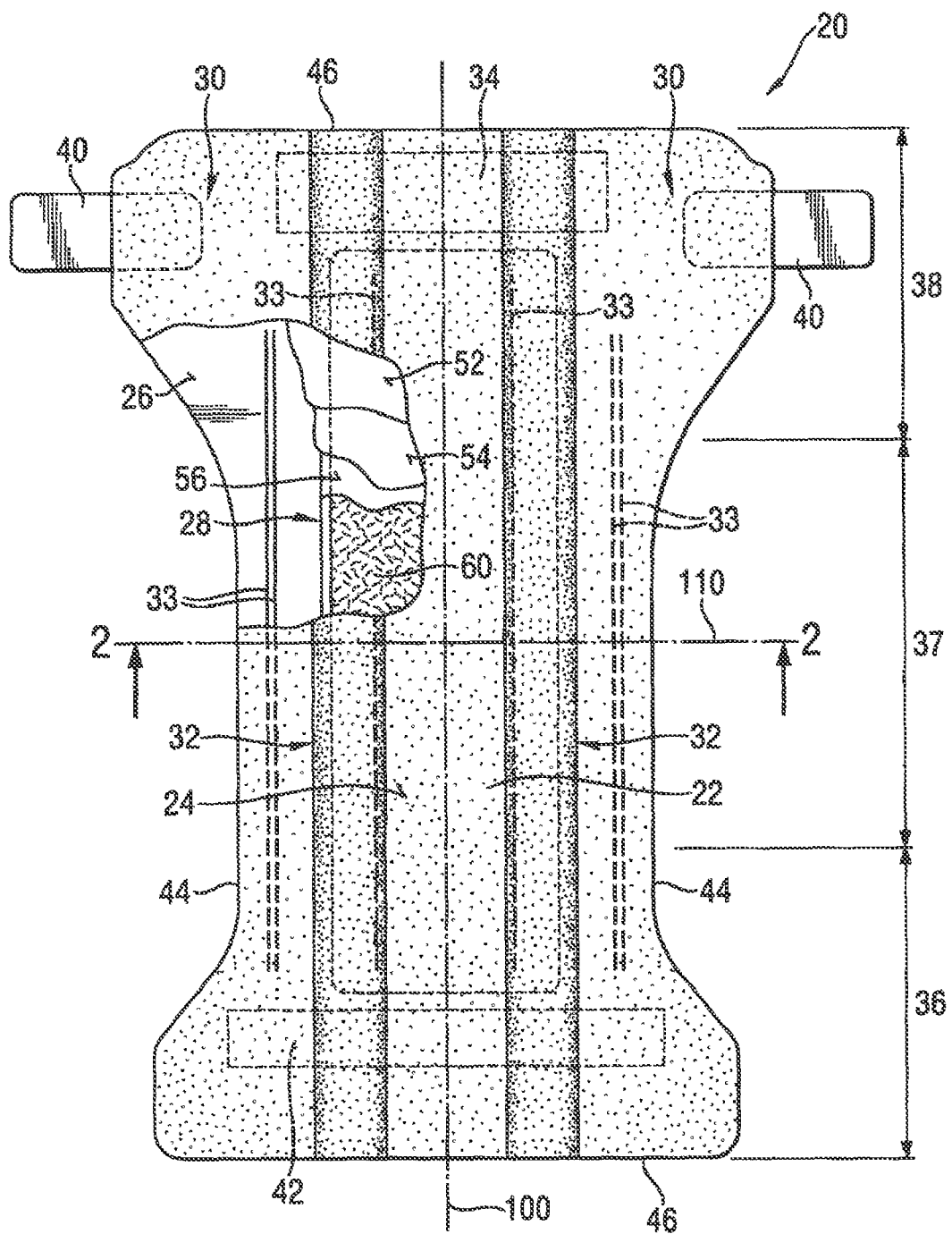
FIG. 1 is a top plan view of a disposable diaper, with the upper layers partially cut away.

All percentages, parts and ratios are based upon the total weight of the compositions of the present invention, unless otherwise specified. All such weights as they pertain to listed ingredients are based on the active level and therefore do not include solvents or by-products that may be included in commercially available materials, unless otherwise specified. All molecular weights as used herein are weight average molecular weights expressed as grams/mole, unless otherwise specified.

Definitions

"Material for acquisition of liquids" and "liquid acquisition material" are used herein interchangeably.

"Absorbent article" refers to devices that absorb and contain liquid, and more specifically, refers to devices that may be placed against or in proximity to the body of the wearer to absorb and contain the various exudates discharged from the body. Absorbent articles include but are not limited to diapers, adult incontinent briefs, training pants, diaper holders and liners, sanitary napkins and the like. Absorbent articles also include wipes, such as household cleaning wipes, baby wipes, and the like "Disposable" is used herein to describe articles that are generally not intended to be laundered or otherwise restored or reused i.e., they are intended to be discarded after a single use and, possibly, to be recycled, composted or otherwise disposed of in an environmentally compatible manner.

"Disposed" is used to mean that an element(s) is formed (joined and positioned) in a particular place or position as a unitary structure with other elements or as a separate element joined to another element.

"Diaper" refers to an absorbent article generally worn by infants and incontinent persons about the lower torso.

The terms "thickness" and "caliper" are used herein interchangeably.

"Attached" or "Joined" encompasses configurations whereby an element is directly secured to another element by affixing the element directly to the other element, and configurations whereby an element is indirectly secured to another element by affixing the element to intermediate member(s) which in turn are affixed to the other element.

"Comprise," "comprising," and "comprises" is an open ended term that specifies the presence of what follows e.g. a component but does not preclude the presence of other features, elements, steps or components known in the art, or disclosed herein.

The term "hydrophilic" describes fibers or surfaces of fibers, which are wettable by aqueous fluids (e.g. aqueous body fluids) deposited on these fibers. Hydrophilicity and wettability are typically defined in terms of contact angle and the strike through time for the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

The terms "fiber" and "filament" are used interchangeably. The terms "nonwoven", "nonwoven fabric" and "nonwoven web" are used interchangeably.

The term "electrolyte" means an ionic substance which increases the electrical conductivity of water when dissolved in water.

Cellulosic Fibers

The term "individualized, crosslinked fibers", refers to fibers that have primarily intrafiber chemical crosslink bonds. That is, the crosslink bonds are primarily between polymer (e.g. cellulose) molecules of a single fiber, rather than between polymer molecules of separate fibers.

The term "cellulosic fiber" is a collective term for fibers made from natural cellulose, from regenerated cellulose or from cellulose esters. Cellulosic fibers from natural cellulose can be e.g. seed fibers or bast fibers. Regenerated cellulose can be made e.g. by dissolving and re-precipitating cellulose. Cellulosic fibers of diverse natural origin are applicable to the invention. Digested fibers from softwood, hardwood or cotton linters are preferably utilized. Fibers from Esparto grass, bagasse, kemp, flax, and other ligneous and cellulosic fiber sources may also be utilized as raw material in the invention. The fibers may be supplied in slurry, unsheeted or sheeted form. Fibers supplied as wet lap, dry lap or other sheeted form are preferably rendered into unsheeted form by mechanically disintegrating the sheet, preferably prior to contacting the fibers with the crosslinking agent. Also, preferably the fibers are provided in a wet or moistened condition. Most preferably, the fibers are never-dried fibers. In the case of dry lap, it is advantageous to moisten the fibers prior to mechanical disintegration in order to minimize damage to the fibers. The optimum fiber source utilized in conjunction with this invention will depend upon the particular end use contemplated. Generally, pulp fibers made by chemical pulping processes are preferred. Completely bleached, partially bleached and unbleached fibers are applicable. It may frequently be desired to utilize bleached pulp for its superior brightness and consumer appeal. Wood fibers that have been at least partially bleached are preferred for use in the process of the present invention. For products such as paper towels and absorbent pads for diapers, sanitary napkins, catamenials, and other similar absorbent paper products, it is especially preferred to utilize fibers from southern North America softwood pulp due to their premium absorbency characteristic.

Crosslinking Agent

Suitable acidic crosslinking agents according to the invention include agents having at least three acidic groups per molecule, wherein the acidic groups can react with hydroxyl groups of cellulosic fibers to form ester bonds. At least two of the acidic groups of one crosslinking agent molecule may react with hydroxyl groups of at least two cellulosic fiber molecules. The reaction may occur between two cellulose molecules of the same fiber to form intra-fiber ester bonds. One suitable example of an acidic crosslinking agent is a polymer having a plurality (i.e. three or more) of acidic functional groups. Acidic functional groups may be for example carboxylic acid, sulfonic acid, or phosphoric acid groups. In one embodiment, the acidic functional groups include carboxylic acid groups. The polyacrylic acid polymers and copolymers described below may be used as acidic crosslinking agents alone or in combination with other polycarboxylic acids such as, for example, citric acid.

The acidic cross-linking agent may be a homopolymer, obtainable from a single type of monomer, wherein the monomer has at least one acidic group. The acidic cross-linking agent may also be a copolymer obtainable from at least two different types of monomers, wherein at least one type of monomer has at least one acidic group and further types of monomers may have no acidic groups. The acidic crosslinking agent may be derived from natural or from synthetic sources. Suitable monomers containing acid groups include, for example, acrylic acid, methacrylic acid, crotonic acid, maleic acid, maleic acid monoesters. Acrylic acid polymers, i.e. polymers obtainable by polymerizing acrylic acid or by co-polymerizing acrylic acid with at least one other monomer different from acrylic acid, may also be suitable. Co-monomers that are not substituted with acid groups include, for example, acrylamide, methacrylamide, alkyl acrylamide, dialkyl acrylamide, alkyl methacrylamide, dialkyl methacrylamide, alkyl acrylate, alkyl methacrylate, vinylcaprolactone, vinylpyrrolidone, vinyl ester, vinyl alcohol, wherein the alkyl groups of these monomers are C1 to C10 alkyl groups; or C1, C2, C3, or C4 alkyl groups. The alkyl groups may be linear or branched.

Acidic crosslinking agents include polyacrylic acid polymers, copolymers of acrylic acid, and mixtures thereof. Particularly suitable examples of polyacrylic acid crosslinking agents include copolymers of polyacrylic acid and maleic acid and the low molecular weight monoalkyl substituted phosphinate and phosphonate copolymers described in U.S. Pat. No. 5,256,746 to Blankenship, et al. These polymers may be especially suitable for crosslinking individualized cellulose fibers as described herein and may exhibit non-negative effects on cellulose brightness when used in a crosslinking process. Also, these polymeric acidic crosslinking agents may exhibit a positive influence on the absorption capacity of the resulting crosslinked cellulosic fibers due to a lower glass transition temperature when compared to monomeric acidic crosslinking agents such as, e.g., citric acid. Polyacrylic acid polymers may be made by polymerizing acrylic acid  to form the repeating chain

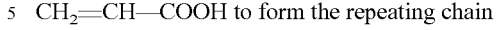

wherein M is an alkali metal, ammonium or hydrogen. In the final, crosslinked cellulosic fibers, M may be hydrogen or at least predominantly hydrogen without metal ions or metal ions present only in such minor amounts that they do not significantly reduce the cation reducing capacity of the material. Polymers of this type are available, for example, from the Rohm and Haas Company. The molecular weights of exemplary copolymers may range from 500-40,000 or even from about 1,000 to about 20,000. The weight ratio of acrylic acid to maleic acid may range from about 10:1 to about 1:1 or even from about 5:1 to 1.5:1. A particularly preferred copolymer may contain about 65% by weight acrylic acid and 35% by weight maleic acid. Another group of acrylic acid copolymers that may be applicable to this invention are the low molecular weight monoalkyl substituted phosphinate and phosphonate copolymers described in U.S. Pat. No. 5,256,746. These copolymers may be especially suitable, since they provide fibers with high levels of absorbency, resiliency and brightness, and are generally safe and non-irritating to human skin. These copolymers may be prepared with hypophosphorus acid and its salts (commonly sodium hypophosphite) and/or phosphorus acid as chain transfer agents. Molecular weights of these types of copolymers may be below 20,000, below 3,000, and even between about 1,000 and 2,000.

The molecular weight of the polymeric, acidic crosslinking agents suitable for use in certain embodiments may be from 500 to 40,000 or even from 1,000 to 20,000. In case of copolymers of acrylic acid, the weight ratio of acrylic acid to further monomers (e.g. maleic acid) can range from 10:1 to 1:1, more preferably from 5:1 to 1.5:1.

Crosslinking of Cellulosic Fibers

In certain embodiments, the crosslinked cellulosic fibers and the method of making them may be those described in PCT Pub. No. WO 95/34710 to Herron, et al. In certain embodiments, the individualized, crosslinked cellulosic fibers may have an effective amount of the polymeric acid crosslinking agent reacted with the fibers in the form of intra-fiber crosslink bonds. As used herein, "effective amount of crosslinking agent" refers to an amount of crosslinking agent sufficient to provide an improvement in at least one significant absorbency property of the fibers themselves and/or absorbent structures containing the individualized, crosslinked fibers, relative to conventional, uncrosslinked fibers. One example of a significant absorbency property is drip capacity, which is a combined measurement of an absorbent structure's fluid absorbent capacity and fluid absorbency rate as described in WO 95/34710. The crosslinked cellulosic fibers may have, for example, from 1 wt. % to 50 wt. % or from 5 wt. % to 30 wt. %, or from 10 wt. % to 20 wt. % crosslinking agent, calculated on a dry fiber basis, reacted with the fibers. The crosslinking agent may be contacted with the fibers in a liquid medium, under such conditions that the crosslinking agent penetrates into the interior of the individual fiber structures. However, other methods of crosslinking agent treatment, including spraying or spray and press, dip and press, etc., of the fibers while in individualized, fluffed form, or sheeted form are also contemplated herein.

Once the fibers are treated with crosslinking agent (and catalyst if one is used), the crosslinking agent may be reacted with the fibers in the substantial absence of inter-fiber bonds, i.e., while inter-fiber contact is maintained at a low degree of occurrence relative to unfluffed pulp fibers, or the fibers are submerged in a solution that does not facilitate the formation of inter-fiber bonding. This may result in the formation of crosslink bonds which are intra-fiber in nature. Under these conditions, the crosslinking agent may react predominantly to form crosslink bonds between hydroxyl groups of a single cellulose chain or between hydroxyl groups of proximately located cellulose chains of a single cellulosic fiber. Although not presented or intended to limit the scope of the invention, it is believed that the acid groups on the acidic polymeric crosslinking agent react with the hydroxyl groups of the cellulose to form ester bonds. The formation of ester bonds, believed to be the desirable bond type providing stable crosslink bonds, is favored under acidic reaction conditions. Therefore, acidic crosslinking conditions, i.e., pH ranges of from about 1.5 to about 5, may be present in certain embodiments. The fibers may be mechanically defibrated into a low density, individualized, fibrous form known as "fluff" prior to reaction of the crosslinking agent with the fibers. Mechanical defibration may be performed by a variety of methods which are presently known in the art.

The crosslinked cellulosic fibers may have unique combinations of stiffness and resiliency, which may allow absorbent structures made from the fibers to maintain high levels of absorptivity, and exhibit high levels of resiliency and an expansionary responsiveness to wetting of a dry, compressed absorbent structure. In addition to having the levels of crosslinking within the stated ranges, the crosslinked fibers may be characterized as having water retention values ("WRVs") of up to 100, e.g. less than about 60, between about 25 to about 50, or even between about 30 and about 45. The WRV of a particular fiber may be indicative of the level of crosslinking for a particular crosslinking chemistry and method. A procedure for measuring WRV is given in WO 95/34710.

Neutralization

Not all acidic groups of the acidic crosslinking polymer undergo ester bond reactions with cellulosic hydroxyl groups, i.e. non-reacted, free acid groups remain in the individualized, crosslinked cellulosic fibers. In certain embodiments, these remaining acid groups may be at least partially neutralized by one or more basic polymers. In certain embodiments the at least partial neutralization may occur when the fibers are wetted. The polymers may comprise at least four, or even eight or more monomeric units. The basic polymers may have a plurality (e.g. three or more) of base groups. Suitable nonlimiting examples of base groups include primary, secondary, tertiary amine groups or quaternary ammonium hydroxide groups. Examples of polymers suitable for use herein include, without limitation, those polymers prepared from polymerizable monomers comprising base groups or groups that can be converted to base groups after polymerization. Thus, such monomers may include those which contain primary, secondary, and/or tertiary amine groups, or the corresponding phosphines or quaternary ammonium groups. The amount of the basic polymer can be such that the degree of neutralization of the acid groups on the crosslinked cellulosic fiber is from 50% to 100%, from 70% to 100%, from 90% to 100%, or even 100%. In certain embodiments, the degree of neutralization may be controlled by the appropriate selection of the amount of basic polymer. The amount of basic polymer may be, for example from 0.5% to 65 wt. %, from 1% to 50 wt. %, or even from 2% to 40 wt. %, based on the total amount of the material. The basic polymer may be used as neutralizing agent alone or in combination with other, water soluble, organic or inorganic non-polymeric bases. In certain embodiments, base groups of the basic polymer may be amine groups such as, for example, primary, secondary, or tertiary amine groups.

The basic polymer may be a homopolymer, obtainable from a single type of monomer, wherein the monomer has at least one base group. The basic polymer may be a copolymer obtainable from at least two different types of monomers, wherein at least one type of monomer has at least one base group and further types of monomers have no base groups. The basic polymer may be derived from natural (e.g. comprising nucleobases) or synthetic sources. The basic polymers may also be random, graft, or block copolymers, and may have linear or branched architectures. Suitable monomers containing base groups include, but are not limited to, vinylamine, allylamine, diallylamine, ethyleneimine (aziridine), 4-aminobutene, alkyl oxazolines, 5-aminopentene, carbodiimides, formaldazine, melamine, dialkylaminoalkyl acrylate, dialkylaminoalkyl methacrylate, dialkylaminoalkyl acrylamide, dialkylaminoalkyl methacrylamide, vinylguanidine, allylguanidine and the like, as well as their secondary or tertiary amine derivatives, e.g. N-monoalkyl- or N,N-di-lkyl compounds with from 1 to 4 carbon atoms.

Basic polymers derived from natural sources include, for example, diethyl amino ethyl ("DEAE") cellulose, polyethyleneimine ("PEI") cellulose, amino ethyl cellulose, triethyl amino ethyl cellulose, guanidoethyl cellulose, paraminobenzyl cellulose, ECTEOLA cellulose (triethanolamine coupled to cellulose through glyceryl and polyglyceryl chains), benzoylated DEAE cellulose, and benzoylated-naphthoylated DEAE cellulose prepared by conventional techniques. DEAE cellulose, for example, can be prepared by treating cellulose with a solution of 2-(diethylamino) ethyl chloride.

Synthetic basic polymers include, for example, poly(vinylamine), poly(allyl-amine), polyethylenimine, poly(dialkylaminoalkyl acrylamide), poly(dialkylaminoalkyl methacrylamide), poly(dialkylaminoalkyl acrylate), poly(dialkylaminoalkyl methacrylate) or polymeric resins containing quaternary ammonium hydroxide groups. Basic polymers may be prepared from at least one monomer having the general structure:

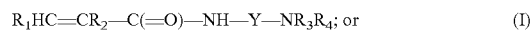

$$R_1HC=CR_2-C(=O)-NH-Y-NR_3R_4; \text{ or} \quad (I)$$

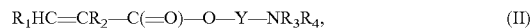

$$R_1HC=CR_2-C(=O)-O-Y-NR_3R_4, \quad (II)$$

wherein $R_1$ and $R_2$, independently, are selected from the group consisting of hydrogen and methyl, Y is a divalent organic radical that can be linear or branched having 1 to 8 carbon atoms, and $R_3$ and $R_4$, independently, are alkyl radicals having 1 to 4 carbon atoms. $R_1$ may be hydrogen, $R_2$ may be hydrogen or methyl, Y may have 2 or 3 carbon atoms, and $R_3$ and $R_4$ may be the same and have 1 or 2 carbon atoms. Further nonlimiting examples of basic polymers are poly (vinylguanidine) and poly(allylguanidine).

In certain embodiments, basic polymers may include a variety of water-insoluble, but water-swellable polymers. The basic polymers are typically lightly crosslinked polymers that contain a multiplicity of base functional groups, such as primary, secondary and/or tertiary amines; or the corresponding phosphines. The polymers may be rendered water-insoluble, but water-swellable, by a relatively low degree of crosslinking. This may be achieved by including the appropriate amount of a suitable crosslinking monomer during the polymerization reaction. Examples of crosslinking monomers include N,N'-methylenebisacrylamide, ethylene glycol di(meth)acrylate, trimethylolpropane tri(meth)acrylate, triallylamine, diaziridine compounds, and the like. Alternatively, the polymers can be crosslinked after polymerization by reaction with a suitable crosslinking agent such as di- or polyhalogenated compounds and/or di- or poly-epoxy compounds. Examples include diiodopropane, dichloropropane, ethylene glycol diglycidyl ether, and the like.

Another exemplary basic polymer is crosslinked divinylbenzene/styrene copolymer containing quaternary ammonium groups in its hydroxide form, e.g. AMBERLYST A26 OH of Rohm and Haas, or any other kind of weak base or strong base anion exchange polymer.

The basic polymer may be of one type (i.e. homogeneous), however, mixtures of base polymers may be used in certain embodiments. For example, mixtures of polyethylenimine (which may be crosslinked) and polyallylamine (which may be crosslinked) be suitable for use in certain embodiments.

Before neutralizing acidic groups of the crosslinked cellulosic fiber, the basic polymer may be from about 50% to about 100%, about 80% to about 100%, or even from about 90% to about 100%, in the un-neutralized base form. In order to potentially improve the electrolyte concentration reducing capacity of the liquid acquisition material, it may be desirable to provide a basic polymer that exhibits a relatively high amount of amine groups per gram of dry polymer. In certain embodiments, the amine group density of the basic polymer component may be at least 4 milliequivalents per gram ("meq/g"), at least 6 meq/g, at least 10 meq/g, at least about 15 meq/g, and even at least about 20 meq/g.

In order to further increase the potential improvement of the electrolyte concentration reduction capacity of the liquid acquisition material, it may be desirable to provide a material comprising approximately equal equivalents of acid groups and base groups. However, it may be desirable to have somewhat more equivalents of acid groups or of base groups, e.g., to compensate for differences in pK, to compensate for differences in neutralization, to alter the pH of (for example to acidify) the liquid to be acquired, etc. The approximate electrolyte concentration reducing capacity of the liquid acquisition material of the invention can be calculated from the acid and base strength of the constituent acidic crosslinked cellulosic fiber material and the basic polymer.

In certain embodiments, the electrolyte concentration reducing capacity of the liquid acquisition material of the invention may be at least 0.05 meq/g, at least 0.1 meq/g, or even at least about 0.3 meq/g.

Disposable Absorbent Article

In certain embodiments, a disposable absorbent article comprising the above described material for acquisition of liquids may be provided. For example it may be desirable to provide a disposable absorbent article comprising a liquid pervious topsheet, a liquid impervious backsheet, a liquid storing absorbent core layer comprising super-absorbent material positioned between said topsheet and said backsheet and a liquid acquiring and distributing layer comprising the material for acquisition of liquids described hereinabove. At least part of the liquid acquisition material may be disposed, for example, between the topsheet and absorbent core layer of the disposable absorbent article such that the liquid to be absorbed (e.g. urine) is contacted with the liquid acquisition material before it is contacted with the core layer.

FIG. 1 shows a plan view of a diaper 20. The diaper 20 is shown in its flat out, uncontracted state (i.e., without elastic induced contraction). Portions are cut away to more clearly show the underlying structure of the diaper 20. The portion of the diaper 20 that contacts a wearer is facing the viewer. The diaper 20 may include a liquid pervious topsheet 24 that faces a wearer when the diaper is worn as intended. The chassis 22 of the diaper 20 in FIG. 1 may be configured as the main body of the diaper 20. The chassis 22 may include a liquid impervious backsheet 26. The chassis may also include most or all of the absorbent core 28 encased between the topsheet 24 and the backsheet 26. The chassis may further include side panels 30, leg cuffs 32 and a waist feature 34. The leg cuffs and the waist feature typically comprise elastic members 33. One end portion of the diaper 20 may be configured as the front waist region 36 of the diaper 20. The opposite end portion may be configured as the rear waist region 38 of the diaper 20. An intermediate portion of the diaper 20 may be configured as the crotch region 37, which extends longitudinally between the front and rear waist regions 36 and 38. The crotch region 37 is the portion of the diaper 20 that is generally positioned between the wearer's legs when the diaper 20 is worn as intended. The diaper 20 may have a longitudinal axis 100 and a transverse axis 110. The periphery of the diaper 20 is defined by the outer edges of the diaper 20 in which the longitudinal edges 44 run generally parallel to the longitudinal axis 100 of the diaper 20 and the end edges 46 run generally parallel to the transverse axis 110 of the diaper 20.

For unitary absorbent articles, the chassis 22 comprises the main structure of the diaper with other features added to form the composite diaper structure. The topsheet 24, the backsheet 26, and the absorbent core 28 may be assembled in a variety of well-known configurations. Specific diaper configurations are described generally in U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 24 in FIG. 1 may be fully or partially elasticized or may be foreshortened to provide a void space between the topsheet 24 and the absorbent core 28. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 26 may be joined with the topsheet 24. The backsheet 26 may be configured to prevent exudates absorbed by the absorbent core 28 and contained within the diaper 20 from soiling other external articles that may contact the diaper 20, such as bed sheets and undergarments. Often, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE.

The absorbent core 28 in FIG. 1 generally is disposed between the topsheet 24 and the backsheet 26. The absorbent core 28 may comprise any absorbent material that is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers, absorbent gelling materials, or any other known absorbent material or combinations of materials. The absorbent core may further comprise minor amounts (typically less than 10%) of non-liquid absorbent materials, such as adhesives, waxes, oils and the like. In one embodiment, the core comprises superabsorbent polymers and is air felt free.

Exemplary absorbent structures for use as the absorbent assemblies are described in U.S. Pat. No. 4,834,735, entitled "High Density Absorbent Members Having Lower Density and Lower Basis Weight Acquisition Zones", issued to Alemany et al. on May 30, 1989; and U.S. Pat. No. 5,650,222 entitled "Absorbent Foam Materials For Aqueous Fluids Made From high Internal Phase Emulsions Having Very High Water-To-Oil Ratios" issued to DesMarais et al. on Jul. 22, 1997.

The diaper 20 may also include such other features as are known in the art including front and rear ear panels, waist cap features, elastics and the like to provide better fit, containment and aesthetic characteristics. Such additional features are well known in the art and are described in U.S. Pat. No. 3,860,003 entitled "Contractable side portions for disposable diaper" issued to Buell et al. on Jan. 14, 1975 and U.S. Pat. No. 5,151,092 entitled "Absorbent article with dynamic elastic waist feature having a predisposed resilient flexural hinge" issued to Buell et al. on Sep. 29, 1992.

In order to keep the diaper 20 in place about the wearer, the waist regions 36 and 38 may include a fastening system comprising fastening members 40 attached to the rear waist region 38. In one embodiment the fastening system further comprises a landing zone 42 attached to the front waist region 36. The fastening member is attached to the front waist region 36, often to the landing zone 42, to form leg openings and an article waist. Diapers 20 according to the present invention may be provided with a re-closable fastening system or may alternatively be provided in the form of pant-type diapers. The fastening system and any component thereof may include any material suitable for such a use, including but not limited to plastics, films, foams, nonwoven webs, woven webs, paper, laminates, fiber reinforced plastics and the like, or combinations thereof. In some embodiments, the materials making up the fastening device are flexible. The flexibility is designed to allow the fastening system to conform to the shape of the body and thus, reduces the likelihood that the fastening system will irritate or injure the wearer's skin.

FIG. 2 shows a cross-sectional view of FIG. 1 taken in the transverse axis 110. Starting from the wearer facing side the diaper comprises the topsheet 24, the components of the absorbent core 28, and the backsheet 26. An acquisition system 50 is disposed between the topsheet 24 and the backsheet 26, preferably between the topsheet 24 and the absorbent core 28. The acquisition system 50 may comprise an upper acquisition layer 52 facing towards the wearer and a lower acquisition layer 54.

In certain embodiments, the liquid acquisition system 50 may comprise the liquid acquisition material. The liquid acquisition material may be disposed either in the upper acquisition layer 52 or in the lower acquisition layer 54 or in both. In certain embodiments the upper acquisition layer 52 comprises a nonwoven fabric and the lower acquisition layer 54 comprises the liquid acquisition material. In certain embodiments, both the upper and lower acquisition layers comprise the liquid acquisition material. When the acquisition system 50 comprises a non-woven fabric, the non-woven fabric may be hydrophilic. In certain embodiments, the acquisition layer may be in direct contact with the absorbent core 28.

The storage layer 60 may be wrapped by a core wrap material. In certain embodiments, the core wrap material may comprise a top layer 56 and a bottom layer 58. The top layer 56 and the bottom layer 58 may include a non-woven material. One useful nonwoven material is a so-called SMS material, which is commonly known in the art as a three-layer material comprising a spunbond layer, a meltblown layer, and another spunbond layer. The top layer 56 and the bottom layer 58 may be provided from two or more separate sheets of materials or they may be provided from a unitary sheet of material. Such a unitary sheet of material may be wrapped around the storage layer 60, e.g. in a C-fold. The top layer 56 and the bottom layer 58 may also be joined to each other, for example along their periphery. In certain embodiments, both layers may be joined along their longitudinal and/or transversal peripheries. The joining can be achieved my multiple means well known in the art, e.g. by adhesive means, using a continuous or a discontinuous pattern, for example a linear or curvilinear pattern. The storage layer 60 may comprise fibrous materials, mixed with superabsorbent polymers and/or absorbent gelling materials. Other materials described above as suitable for the absorbent core 28 may also be included. In one embodiment, the storage layer 60 has reduced amounts of fibrous materials or is free of fibrous materials and the concentration of superabsorbent polymer and/or absorbent gelling materials in the storage layer 60 is at least 40 wt. %, at least 60 wt. % or at least 90 wt. %, based on the total amount of absorbent material in the storage layer 60.

Method of Use

In certain embodiments, a method of reducing the electrolyte concentration of an electrolyte containing aqueous medium is disclosed. The method may comprise contacting an aqueous medium which contains electrolytes with one or more examples of the liquid acquisition material described above.

Method of Making

In certain embodiments, a process for making one or more examples of the liquid acquisition material described above may comprise a) providing a cellulosic based fiber, b) impregnating the fiber with the at least one acidic crosslinking agent and with the at least one basic substance, and c) heating the resulting mixture to temperatures of at least the boiling point of water. Optionally, the resulting crosslinked fiber mixture may be baled, as is commonly known in the art.

EXAMPLES

The materials illustrated in the following examples illustrate specific embodiments of the present invention, but are not intended to be limiting thereof. Other modifications can be undertaken by the skilled artisan without departing from the spirit and scope of this invention.

All exemplified amounts are listed as weight percents and exclude minor materials such as diluents, preservatives, colour solutions, imagery ingredients, botanicals, and so forth, unless otherwise specified. If a trade name is mentioned as ingredient and the respective product is itself a mixture (e.g. a solution, emulsion, dispersion etc.), then the exemplified amount relates to this mixture, unless otherwise specified.

In the following examples, 4 g patches, made of individualized, crosslinked cellulosic fibers are used. The fiber material is made according to Example II of WO 95/34710 except that the crosslinked fibers contain 8 wt. % polyacrylic acid (i.e. 0.32 g of polyacrylic acid are in a 4 g fiber patch), calculated on a dry fiber weight basis, reacted with the fibers in the form of intrafiber crosslink bonds.

Polyallylamine (PAAm) is commercially available as 20 wt. % aqueous solutions. Crosslinked quaternary ammonium hydroxide divinylbenzene/styrene copolymer is commercially available (Amberlyst A-26 OH) as water containing spherical resin beads. Both chemicals are used without further purification. The density of the 20 wt. % aqueous solution of polyallylamine is estimated to be ~1 g/ml.

Different saline (NaCl) solutions from 0.8 to 0.9 wt. % are prepared and their conductivity measured. Within this concentration range, there is an almost linear relationship between conductivity and NaCl concentration. This relationship is used as reference to determine the NaCl concentration of the test samples by measuring the conductivity of the test samples.

The conductivity of 0.9 wt. % saline solutions before and after contact with the test material is measured, corrected for the conductivity effect of the basic material (polyallylamine or Amberlyst A-26 OH, respectively) and corrected for the dilution effect of water. The decrease in NaCl concentration (desalting effect) of the test samples is determined from the conductivity/concentration relationship.

Conductivity Measurement Method
Equipment:
Conductivity Meter: WTW LF 320
Stirrer and Hot Plate: IKA RH-KT/C
Eppendorf Pipette The fiber patch is washed several times with distilled water and dried at 50° C. to remove all extractable components that might influence the conductivity measurements.

All conductivity measurements are carried out at room temperature or at 37° C. but the conductivity meter is used in "auto-correlation" mode so that the given conductivities are automatically correlated to 25° C. 4 g PAA-crosslinked cellulosic fiber pads are merged into 200 ml 0.9 wt. % saline (NaCl) solution and after 5 minutes of stirring the conductivity is measured. This conductivity is set as the base for the series of measurements and for the following calculations.

Example 1

4 g washed and dried polyacrylic acid crosslinked cellulosic fiber pad is merged into 200 ml 0.9 w % saline solution at room temperature, and after 5 min of manually stirring the conductivity is measured. Polyallylamine (PAAm) is added. The mixture is stirred and the conductivity is observed. From the conductivity change the concentration change of the NaCl solution is calculated and corrected for dilution effects.

| Amount PAAm added | 0.28 g |
| Difference in conductivity | −0.95 mS/cm |
| Effective NaCl reduction | −0.051 wt. % |

Example 2

4 g washed and dried polyacrylic acid crosslinked cellulosic fiber pad is merged into 200 ml 0.9 w % saline solution at room temperature and after 5 min of manually stirring the conductivity is measured. Amberlyst A-26(OH) is added. The mixture is stirred and the conductivity is observed. From the conductivity change the concentration change of the NaCl solution is calculated and corrected for dilution effects.

| Amount Amberlyst A-26(OH) added | 1.8 g |
| Difference in conductivity | −1.08 mS/cm |
| Effective NaCl reduction | −0.065 wt. % |

Example 3

4 g washed and dried polyacrylic acid crosslinked cellulosic fiber is strongly mixed for 10 minutes with 1.5 g Amberlyst A-26(OH) and then gently compressed with a pistil and 0.3 psi. A 0.9 wt. % saline solution is tempered to 37° C. and 100 ml of the saline solution is poured in one gush on top the cellulosic fiber pad/A-26(OH) mixture to allow the liquid to flow through the pad and the solution was collected afterwards. This is repeated two more times and the conductivity before and afterwards as well as the amount of liquid is measured.

From the conductivity change the amount of absorbed NaCl is determined to be 1.249 mmol after 3 gushes of 100 ml (280 ml recovered).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

All documents cited in the Detailed Description of the Invention are, in relevant part, incorporated herein by reference; the citation of any document is not to be construed as an admission that it is prior art with respect to the present invention. To the extent that any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making a material for acquisition of liquids, said material comprising individualized, crosslinked cellulosic fibers including an effective amount of at least one acidic crosslinking agent reacted with said fibers in intra-fiber crosslink ester bond form, said acidic crosslinking agent being a polymer comprising a plurality of acidic functional groups; and at least one basic polymer, said method comprising:
   a. providing a cellulosic based fiber,
   b. impregnating the fiber with the at least one acidic crosslinking agent and with the at least one basic polymer, and
   c. heating the resulting mixture to temperatures of at least the boiling point of water;
   d. neutralizing non-reacted, free acid groups in the crosslinked fiber mixture.

2. The method of claim 1, further comprising baling the crosslinked fiber mixture.

3. The method of claim 1, wherein the cellulosic based fiber is provided in slurry or unsheeted form.

4. The method of claim 1, wherein the cellulosic based fiber is provided in wet lap, dry lap, or other sheeted form, the method further comprising mechanically disintegrating the sheet.

5. The method of claim 1, wherein the cellulosic based fiber is selected from the group consisting of digested fibers from softwood, hardwood or cotton linters; fibers from Esparto grass; fibers from bagasse; fibers from kemp; and fibers from flax.

6. The method of claim 1, further comprising moistening the cellulosic based fibers.

7. The method of claim 1, wherein the acidic functional groups are selected from the group consisting of carboxylic acid, sulfonic acid, phosphoric acid, carboxylic acid, and combinations thereof.

8. The method of claim 1, wherein the acidic crosslinking agent is polyacrylic acid, polyacrylic acid copolymers, or a combination thereof.

9. The method of claim 8, wherein the acidic crosslinking agent is a copolymer of polyacrylic acid and maleic acid.

10. The method of claim 8, wherein the acidic crosslinking agent is a copolymer of low molecular weight monoalkyl substituted phosphinate and phosphonate.

11. The method of claim 8, wherein the acidic crosslinking agent is used in combination with one or more other polycarboxylic acids.

12. The method of claim 1, wherein the at least one acidic crosslinking agent is contacted with the cellulosic based fibers in a liquid medium.

13. The method of claim 1, wherein the at least one acidic crosslinking agent is contacted with the cellulosic based fibers by spraying, spray and press, or dip and press processes.

14. The method of claim 1, further comprising mechanically defibrating the cellulosic based fiber into fluff.

15. The method of claim 1, wherein the non-reacted, free acid groups are neutralized when the fibers are wetted.

16. The method of claim 15, wherein the non-reacted, free acid groups are neutralized by a basic polymer.

17. The method of claim 16, wherein the non-reacted, free acid groups are neutralized by a basic polymer in combination with other, water soluble, non-polymeric bases.

18. The method of claim 1, further comprising incorporating the crosslinked fiber mixture into an absorbent article.

19. The method of claim 18, wherein the crosslinked fiber mixture forms at least a part of a liquid acquisition material.

* * * * *